US010376659B2

(12) United States Patent
Nichols

(10) Patent No.: US 10,376,659 B2
(45) Date of Patent: Aug. 13, 2019

(54) PERSONAL CARE VAPORIZER DEVICE FOR THE EYE AREA OF THE FACE

(71) Applicant: Thomas Nichols, Laguna Niguel, CA (US)

(72) Inventor: Thomas Nichols, Laguna Niguel, CA (US)

( * ) Notice: Subject to any disclaimer, the term of this patent is extended or adjusted under 35 U.S.C. 154(b) by 0 days.

(21) Appl. No.: 13/931,398

(22) Filed: Jun. 28, 2013

(65) Prior Publication Data

US 2014/0336565 A1 Nov. 13, 2014

Related U.S. Application Data

(60) Provisional application No. 61/821,089, filed on May 8, 2013.

(51) Int. Cl.
*A61F 9/04* (2006.01)
*A61M 11/04* (2006.01)
*A61M 11/00* (2006.01)
*A61M 21/00* (2006.01)

(52) U.S. Cl.
CPC ......... *A61M 11/042* (2014.02); *A61M 11/005* (2013.01); *A61M 21/00* (2013.01); *A61F 9/04* (2013.01); *A61M 2021/0027* (2013.01); *A61M 2021/0044* (2013.01); *A61M 2021/0066* (2013.01); *A61M 2205/3653* (2013.01); *A61M 2205/8206* (2013.01); *A61M 2210/0606* (2013.01)

(58) Field of Classification Search
CPC ........ A61H 33/12; A61H 35/02; A61H 35/00; A61F 2007/0004; A61F 9/00; A61F 9/0008; A61F 2009/0035; A61F 9/04; A61F 9/026; A61F 9/029; A61M 2210/0606; A61M 2210/0612; A61M 11/00; A61M 2202/03; A61M 11/0042; A61M 11/005; A61M 21/00
USPC .................................. 604/294–296, 298–303
See application file for complete search history.

(56) References Cited

U.S. PATENT DOCUMENTS 3,602,217 A 8/1971 Felton et al.
5,807,357 A * 9/1998 Kang ................... A61M 11/005
604/294
6,155,995 A 12/2000 Lin
(Continued)

*Primary Examiner* — Kevin C Sirmons
*Assistant Examiner* — Leah J Swanson
(74) *Attorney, Agent, or Firm* — Knobbe Martens Olson & Bear LLP

(57) ABSTRACT

A Personal Care Vaporizer Device for the Eye Area of the Face. A treatment chamber formed within the device will encircle the user's eyes and surrounding facial area when the device is positioned over the eye area of the face. A soft gel eyemask element provides maximum comfort for the wearer during treatment. The device introduces therapeutic mist or vapor into the treatment chamber. The mist/vapor is generated from an internal reservoir containing plain water or water mixed with other therapeutic additives. An onboard blower can control the flow rate of the mist/vapor into the treatment chamber. One or more onboard heating elements within the device provide direct heat to the treatment chamber wall(s), and/or to heat the mist/vapor prior to its being introduced into the treatment chamber. Onboard vibration generators apply soothing massaging motion to the user's face when activated.

15 Claims, 10 Drawing Sheets

(56) References Cited

U.S. PATENT DOCUMENTS

| | | |
|---|---|---|
| 7,637,878 B2 | 12/2009 | Lin |
| 2002/0124843 A1* | 9/2002 | Skiba .................... A61M 11/02 128/200.18 |
| 2003/0056281 A1* | 3/2003 | Hasegawa ................ A61F 7/02 2/428 |
| 2004/0050953 A1* | 3/2004 | Terada et al. .............. 239/102.2 |
| 2005/0240162 A1* | 10/2005 | Chen et al. ................... 604/298 |
| 2005/0256433 A1* | 11/2005 | Lin ................................ 601/70 |
| 2006/0200052 A1* | 9/2006 | Lin ................................ 601/70 |
| 2007/0119968 A1* | 5/2007 | Collins et al. ............. 239/102.1 |
| 2012/0004599 A1* | 1/2012 | Nakamura ........... A45D 44/002 604/24 |

* cited by examiner

PERSONAL CARE VAPORIZER DEVICE FOR THE EYE AREA OF THE FACE

This application is filed within one year of, and claims priority to Provisional Application Ser. No. 61/821,089, filed May 8, 2013.

This application is a continuation-in-part of application Ser. No. 29/457,560, filed Jun. 11, 2013, now pending. This application is further a continuation-in-part of application Ser. No. 13/413,491 filed Mar. 6, 2012, now pending, and application Ser. No. 12/079,747, filed Mar. 27, 2008, now U.S. Pat. No. 8,157,753 ("the parent applications").

BACKGROUND OF THE INVENTION

1. Field of the Invention

This invention relates generally to personal skin care devices and methods and, more specifically, to a Personal Care Vaporizer Device for the Eye Area of the Face.

2. Description of Related Art

Skin treatment devices are plentiful. Some pertinent examples of conventional devices and systems in this field are: Mehl, Sr., et al., U.S. Pat. No. 6,090,085, Walker, U.S. Pat. No. 5,098,414, and Burian, U.S. Pat. No. 4,616,122.

Mehl is a "Skin Moisturizing and Buffing Device." The Mehl system combines a handheld facial buffer that has an internal steam generator for creating a stream of steam for emission through the "movable skin contacting assembly" (i.e. the facial buffer head). While the Mehl device does provide a handheld steam buffer, it fails to allow the user the option of either cool vapor or heated steam emitted through the buffer head. Furthermore, the amount of vapor available for use is severely limited due to the entire package being of handheld size. A device providing a large volume liquid reservoir that can emit either heated steam or cool vapor would provide a wider set of benefits to the user.

Walker is a "Steam Device for Cosmetic Skin Treatment." The Walker device does provide a large water reservoir for use in steam emission, but it fails to provide the option of cool vapor.

The Burian "Electrically Heated Facial Sauna Vapor Generating Apparatus," like Walker discloses a large-reservoir, steam-generating facial massage device. Just as with Walker, Burian fails to suggest the generation of cool vapor (in addition to hot steam) for facial application through the massage head. The ability to deliver hot or cool vapor through the massage head allows the user to continue the facial massage while heating and cooling the massage head and skin. If the only option is to deliver steam, then the user must either stop the massage or stop the vapor delivery in the event that the face becomes uncomfortably hot.

In the field of massage or treatment of the face, the following references have been uncovered and are deemed relevant: Lin (I), U.S. Pat. No. 6,155,995, Lin (II), U.S. Pat. No. 7,637,878, Lin (III), U.S. Patent Application Publication No. US2005/0256433, Felton, U.S. Pat. No. 3,602,217, and Chen, U.S. Patent Application Publication No. US2005/0240162 all relate to mask-like apparatus for treating the user's upper face and eye region.

Lin (I) discloses a "Structure of a Multifunctional Eye Mask." The Lin (I) device has an inflatable facemask that provides contact heat and vibrations to the user's face. There is no provision for the generation and application of cool or heated vapor to the user's face.

Lin (II) discloses a "Multi-Functional Eye Massaging Device Having Expandable Body," which like Lin (II) includes an inflatable eyemask with direct heat application and vibration, but does not suggest the introduction of mist or vapor.

Lin (III) introduces a "Centrifugal, Rotating Power Element and A Massaging Device Using the Same," that, like its parents, fails to disclose or hint at the introduction of mist or vapor to the eye area.

Felton discloses an "Eye Treatment Device" for washing a single eye of a user with liquid. The Felton device does not suggest the use of vapor or mist, nor does introduce heat or vibrating massage.

Finally, Chen does disclose a device intended to introduce liquid vapor to the eye area. The Chen "Eye Treatment Device" is actually intended to clean the users eyes and sterilize the users contact lenses (which in the eyes) by application of sterilized, atomized liquid to the eyes. In that the Chen device is focused on eye cleansing, there is no suggestion of the use of vibratory massage, heated mist/vapor, or direct heat to the user's facial area.

SUMMARY OF THE INVENTION

In light of the aforementioned problems associated with the prior devices and methods, it is an object of the present invention to provide a Personal Care Vaporizer Device for the Eye Area of the Face. The device should provide a treatment chamber formed within it that will encircle the user's eyes and surrounding facial area when the device is positioned over the eye area of the face. The device should introduce therapeutic mist or vapor into the treatment chamber. A soft gel (or other soft seal) eyemask element should engage the users face to provide maximum comfort for the wearer during treatment, while also containing the condensed vapor/mist. The mist/vapor is preferably generated from an internal reservoir containing plain water or water mixed with other therapeutic additives. An onboard blower may be provided in order to control the flow rate of the mist/vapor into the treatment chamber. One or more onboard heating elements may also be dispersed within the device to provide direct heat to the treatment chamber wall(s), and/or to heat the mist/vapor prior to its being introduced into the treatment chamber. The device may further be equipped with onboard vibration generators designed to apply soothing massaging motion to the user's face when activated.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a Personal Care Vaporizer Device for the Eye Area of the Face.

Figure 1:
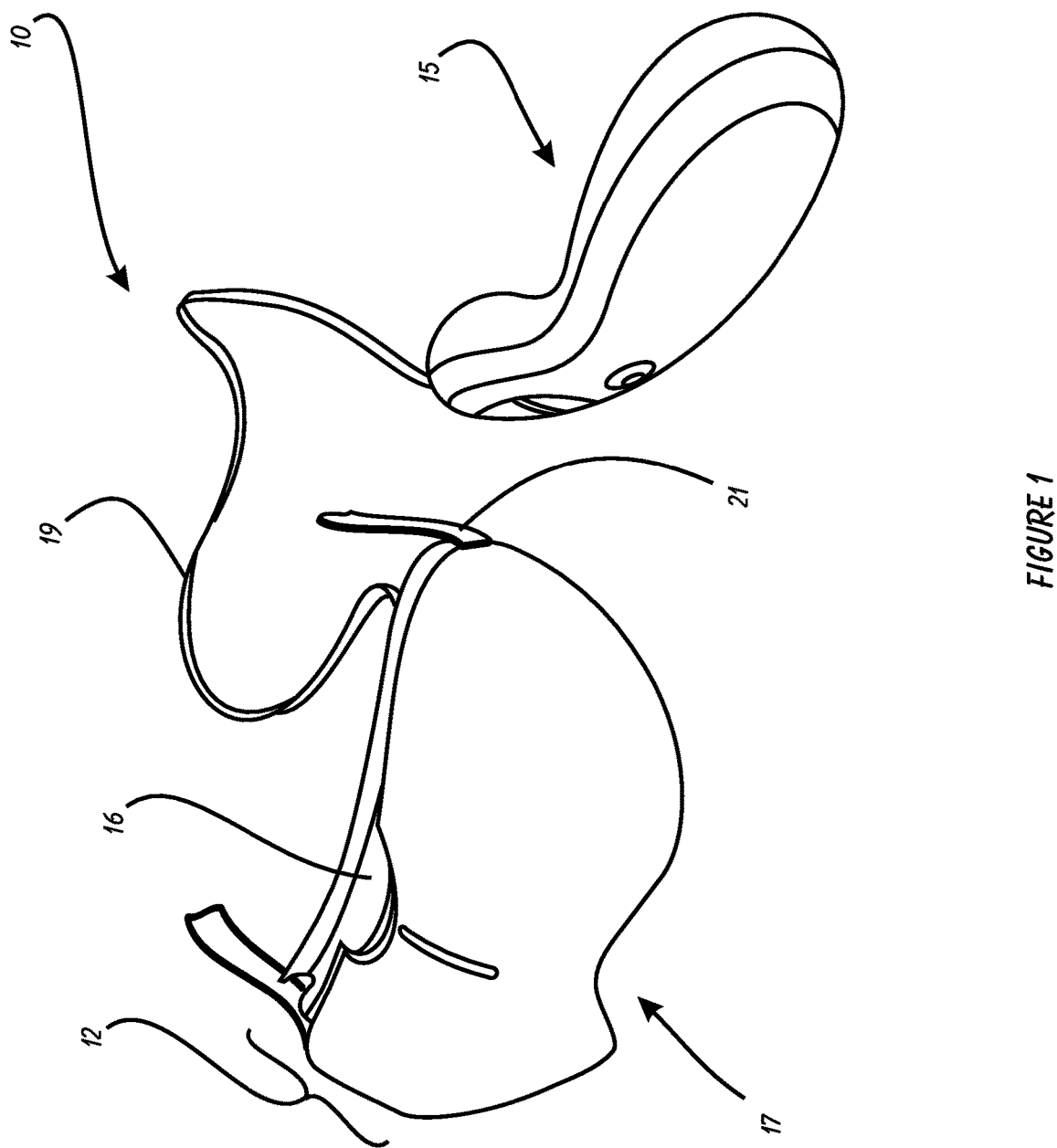
FIG. 1 is a perspective view of a preferred embodiment of the personal care vaporizer device for the eye area of the face of the present invention.

The present invention can best be understood by initial consideration of FIG. 1.[1] FIG. 1 is a perspective view of a preferred embodiment of the personal care vaporizer device for the eye area of the face 10 of the present invention. There are two major components to the device 10—the mask assembly 17 and the handheld control assembly 15. These two assemblies 17, 15 are interconnected by control cable 19 in this version, but in other versions, it is anticipated that a wireless interconnection could be easily implemented. Furthermore, in yet another alternative version, the user control features provided on the control assembly 15 could be integrated into the mask assembly 17 in order to eliminate the separate component and cable.

[1] As used throughout this disclosure, element numbers enclosed in square brackets [ ] indicates that the referenced element is not shown in the instant drawing figure, but rather is displayed elsewhere in another drawing figure.

A strap or other flexible element 21 extends from the mask assembly 17 for the purpose of securing the mask assembly 17 to the users face, just as one might wear a decorative or protective mask. The functional components of the mask assembly 17 are contained within the main housing 12. As will be discussed in more detail below, the user replenishes the fluid within the mask assembly 17 by lifting up the fill port lid 16, which is preferably formed from flexible, pliable material. Now turning to FIG. 2, we can examine the device in more detail.

Figure 2:
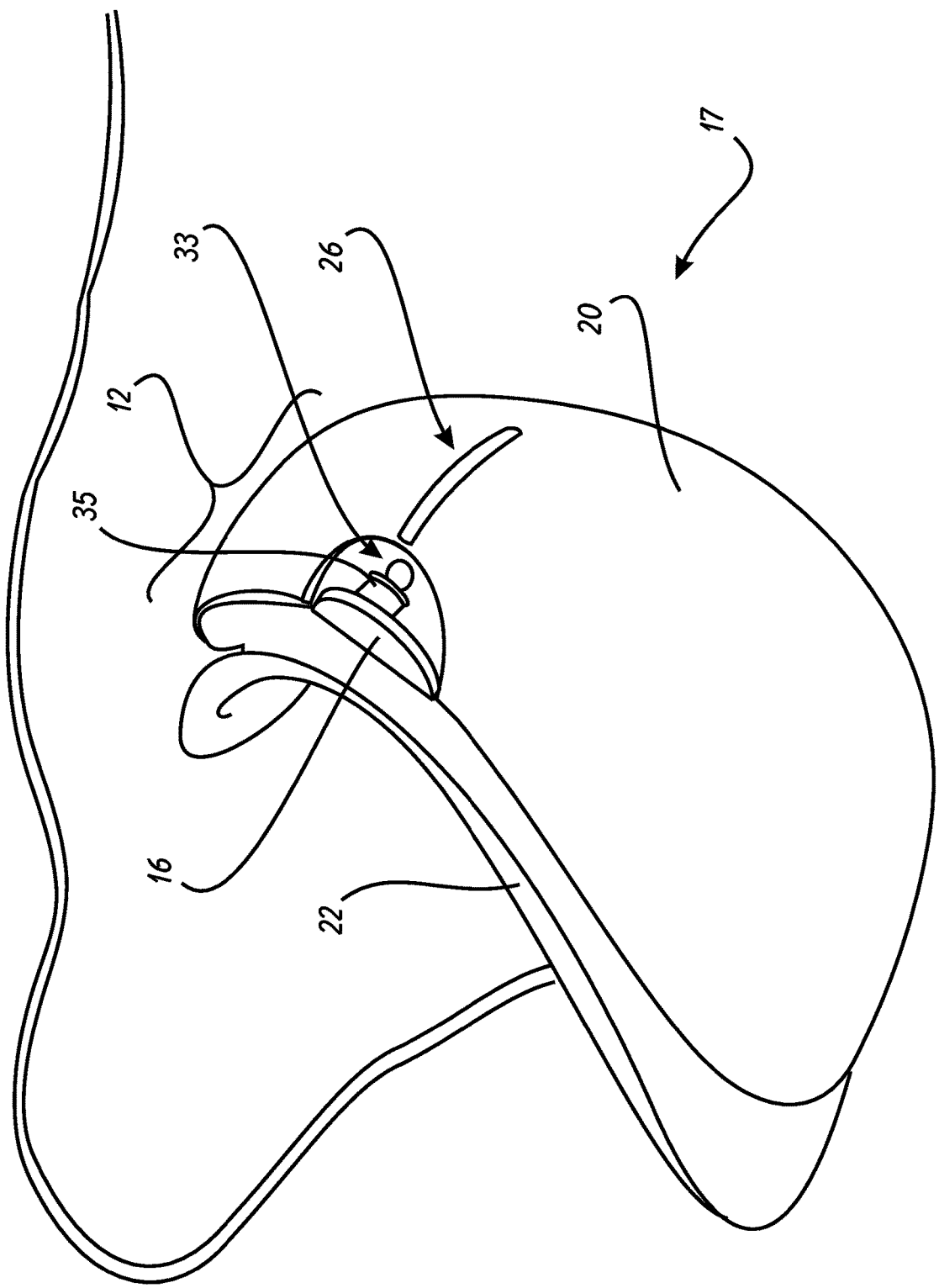
FIG. 2 is a perspective view of the mask assembly of the device of FIG. 1.

FIG. 2 is a perspective view of the mask assembly 17 of the device [10] of FIG. 1. A pliable (neoprene or other material) gasket member 22 is attached to the back-side of the housing 12 (i.e. it will be against the user's face when the mask assembly 17 is attached thereto. The internal components of the main housing 12 are found beneath the front cover 20. The front cover 20 has a fill port 33 formed in it. As discussed above, the user pours or injects fluid into the main housing 12 via the fill port 33. A generally clear liquid level window 26 is formed in the front cover 20 in order to view how much fluid is in the reservoir contained within the main housing 12, as is discussed in more detail below.

Figure 3:
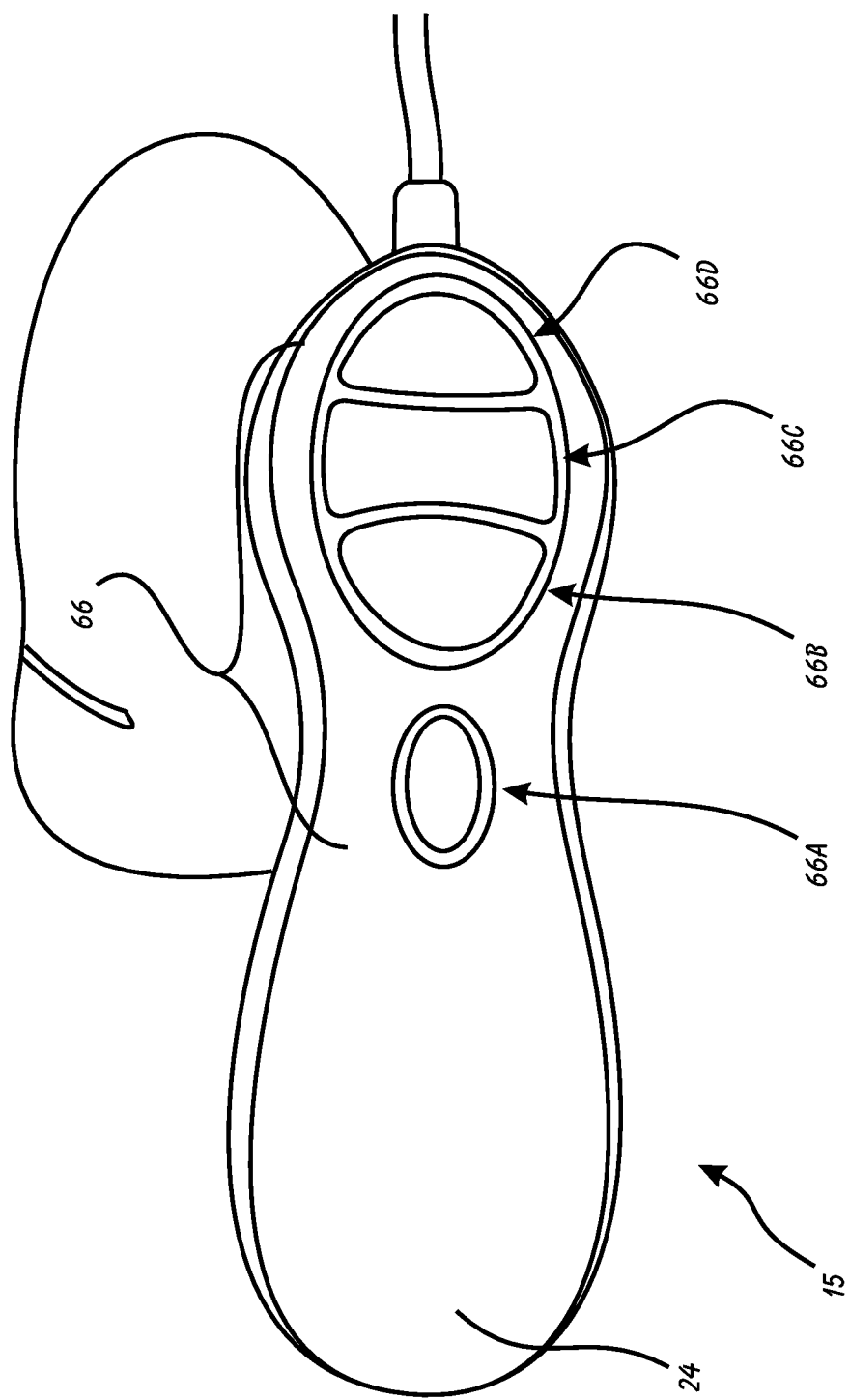
FIG. 3 is a top view of the handheld control assembly of the device of FIG. 1.

The fill port 33 is sealed when not being filled by the fill plug 35 extending from the fill port lid 16. In this version, the fill plug 35 is an integrated feature of the fill port lid 16, and is therefore formed from the same piece of pliable material. FIG. 3 illuminates the features of the other main component of the device [10].

FIG. 3 is a top view of the handheld control assembly 15 of the device [10] of FIG. 1. The assembly 15 is contained within housing 24, and has a plurality of switch buttons 66 dispersed in its outer surface. These switch buttons 66 could be conventional buttons or touch-sensitive pads. In either case, it is expected that they would be liquid-tight to prevent contaminating materials from seeping into the housing 24.

A power switch 66A is used to activate or deactivate the device [10]. Massage control switch button 66B is used to turn the internal massaging vibration feature on and off, as well as selecting the intensity of the vibration (here it is low or high). Heat control switch button 66C is used to turn the internal heater on and off, and to select the intensity. The device may be configured to heat the mist/vapor or the wall(s) of the treatment chamber, or both. The mist control switch button 66D is used to activate the ultrasonic vaporizer (or other method for vaporizing water, such as an ionic element) within the mask assembly [17] so that cool (or warm) vaporized liquid is introduced to the treatment chamber within the mask [17].

Other control buttons may be provided for the following features (in alternative embodiments): airflow control, separate mist heat and treatment area heat controls, mood lighting control, sound/music control, among others.

Figure 4:
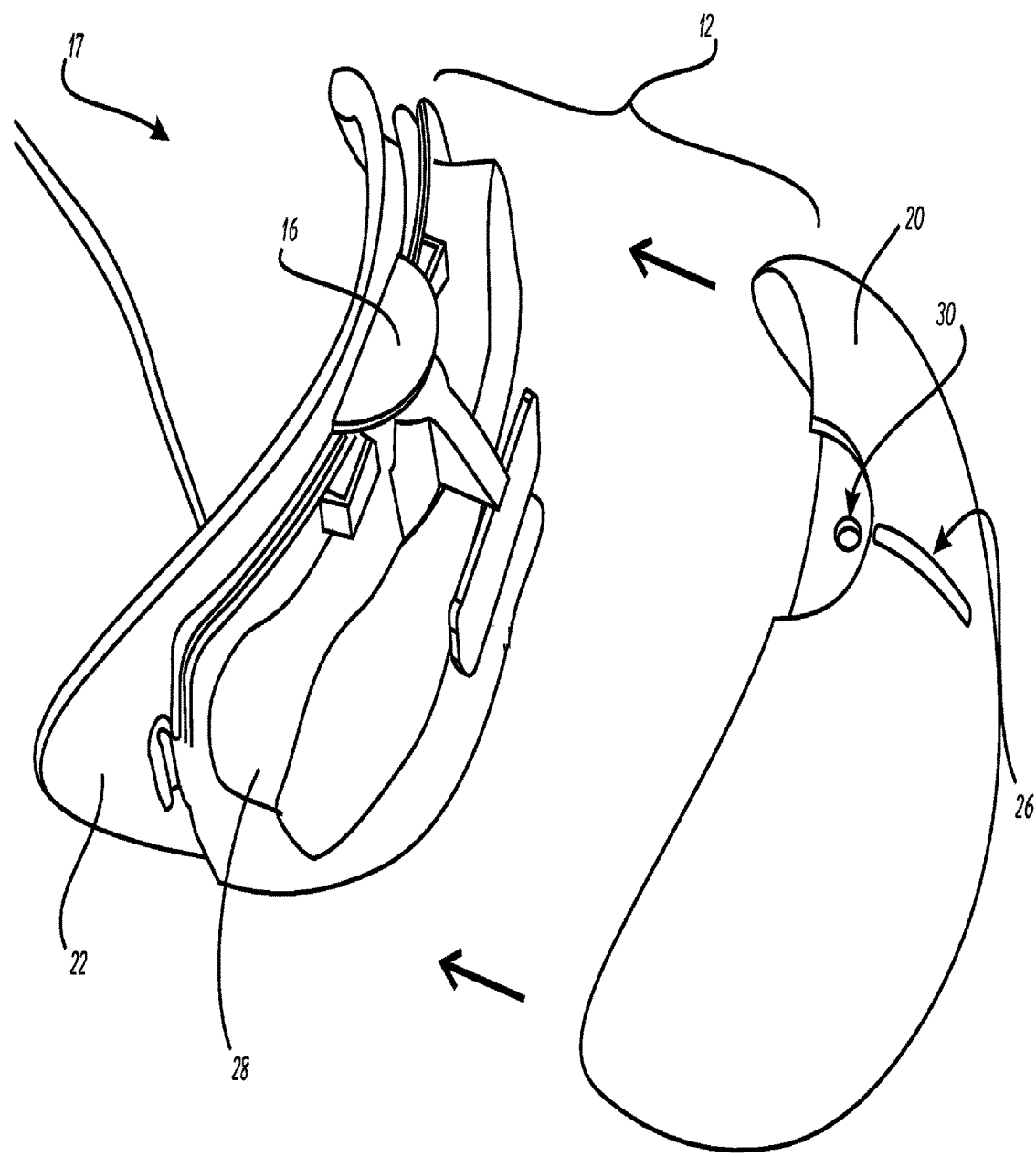
FIG. 4 is a partially exploded perspective view of the mask assembly of FIG. 2.

This version [10] is provided with rechargeable batteries within the handheld control assembly 15. These batteries could be replaced as necessary. In an alternate form, the device [10] may receive its power from a power cord. FIG. 4 introduces the internal components of the mask assembly [17].

FIG. 4 is a partially exploded perspective view of the mask assembly 17 of FIG. 2. The main housing 12 is comprised of the rear housing 28 and its components, and the front cover 20. The gasket member 22 is attached to the back-side of the rear housing member 28. In this version, the fill port lid 16 (and fill port plug [33]) are integral parts of the gasket member 22. The front cover 20 is generally opaque, but is formed with a liquid level window 26 of transparent or translucent material incorporated therein (or just an opening). The fill access aperture 30 is provided so that the fill port [33] can be accessed therethrough. Typically, the control electronics for the device [10] will be contained on a single printed circuit board 29, as shown here, but other conventional approaches could also be used. As shown by the arrows, the front cover 20 attaches over the top of the functional components attached to the rear housing member 28. These components will be discussed in more detail below in connection with FIGS. 5-9.

Figure 5:
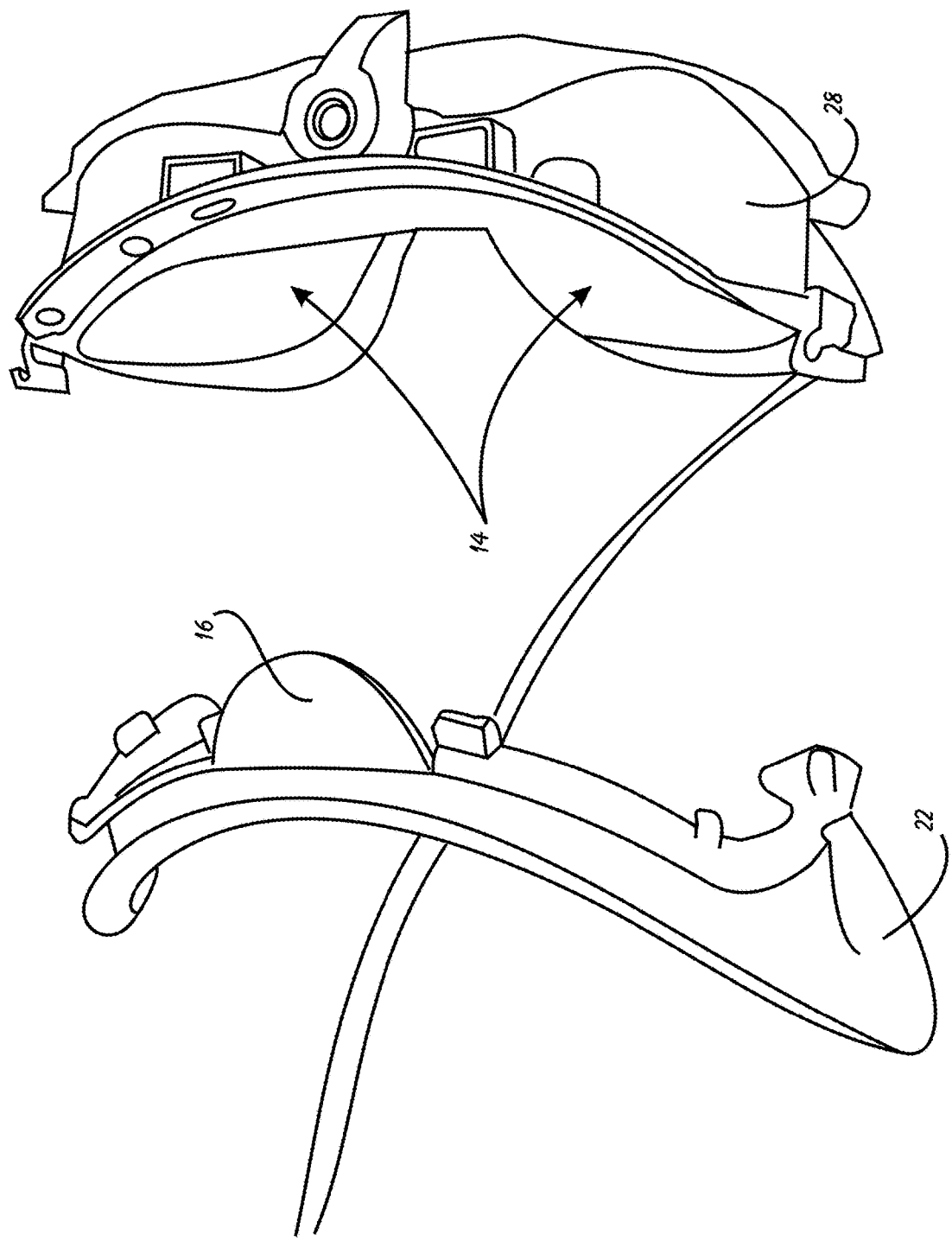
FIG. 5 is a top perspective view of the gasket and rear housing members of the device of FIG. 1.
Figure 6:
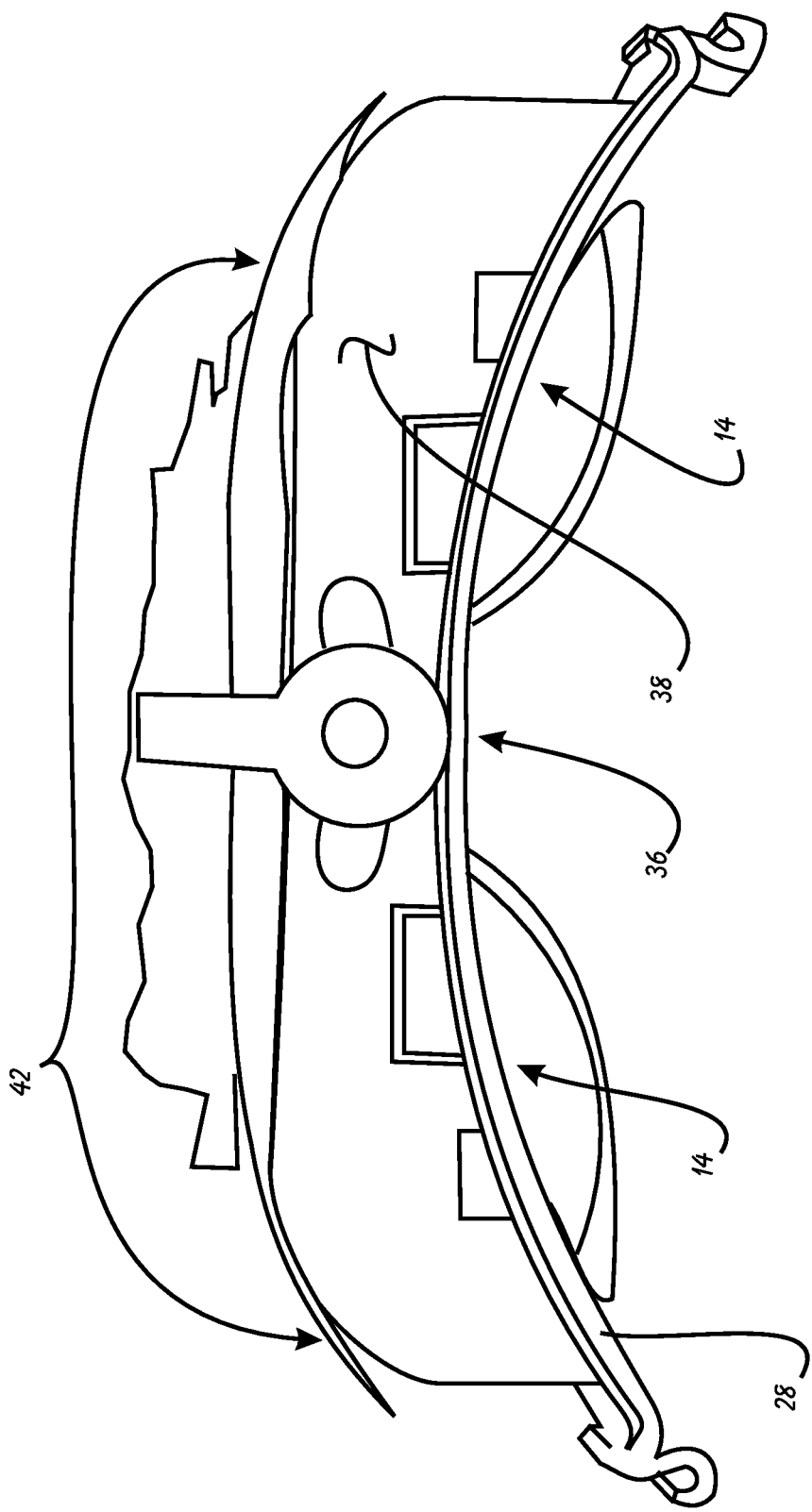
FIG. 6 is a top view of the rear housing member of the device of FIG. 1.
Figure 7:
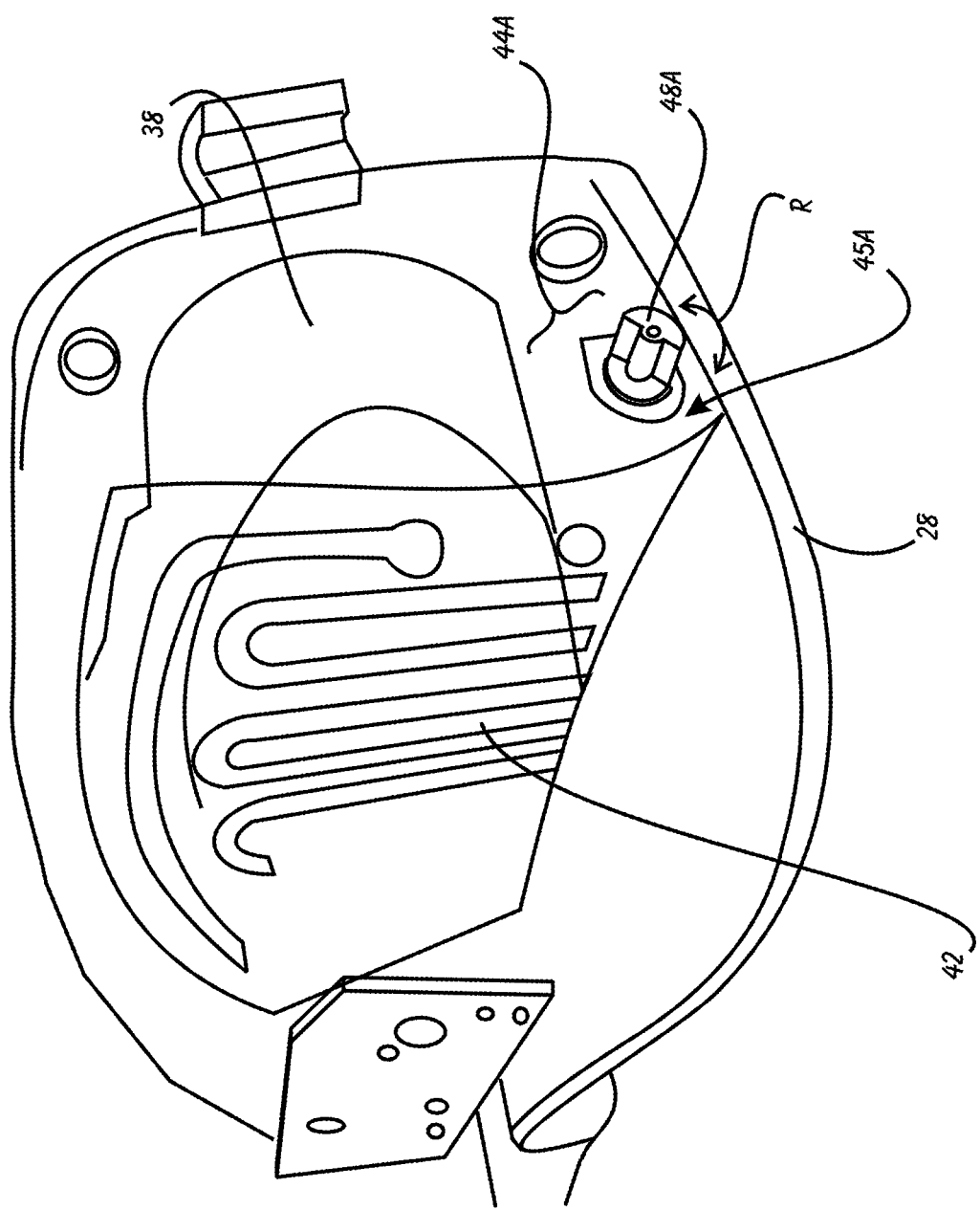
FIG. 7 is a partial right perspective view of the rear housing member of the device of FIG. 1.
Figure 8:
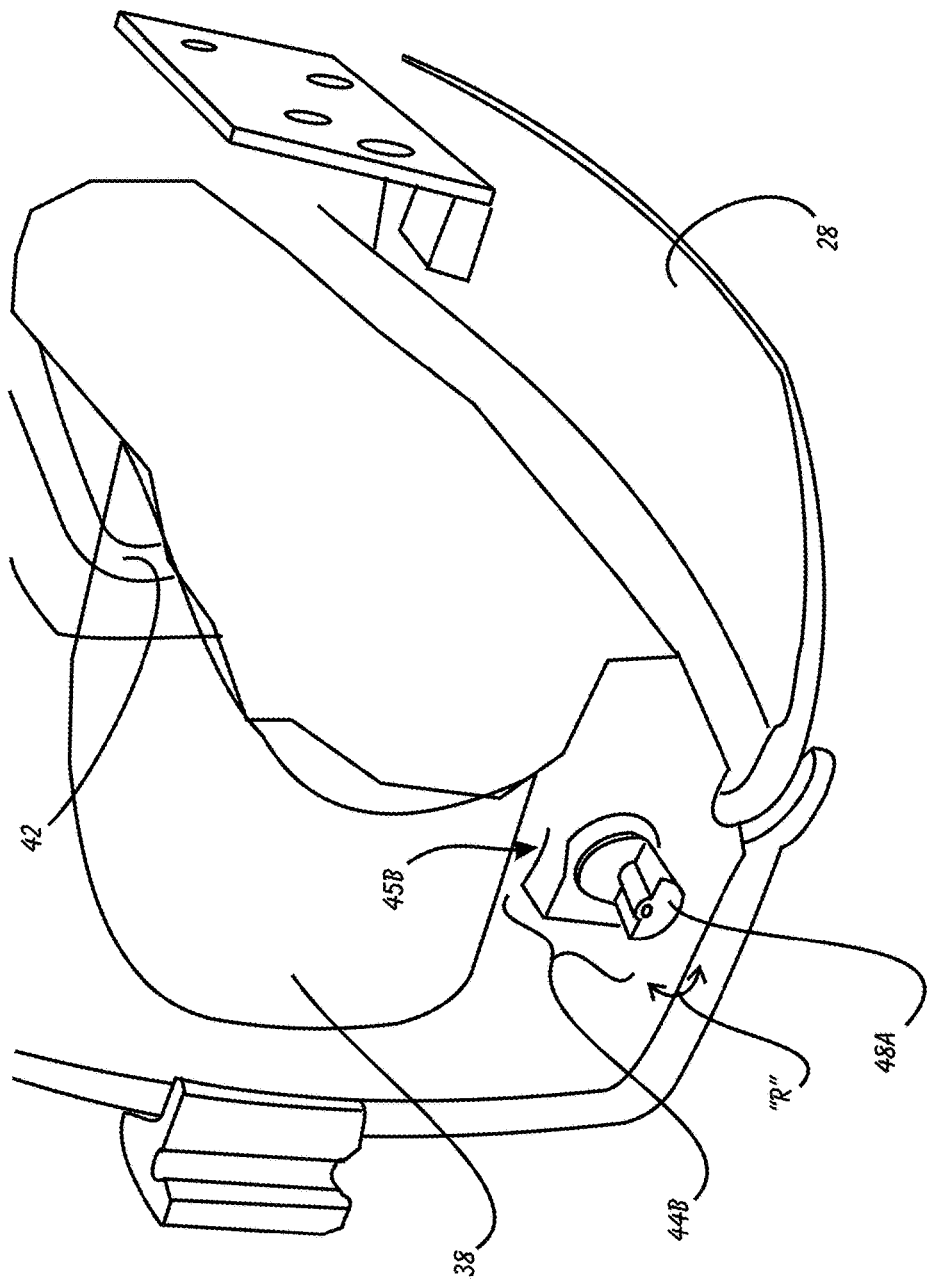
FIG. 8 is a partial left perspective view of the rear housing member of the device of FIG. 1.
Figure 9:
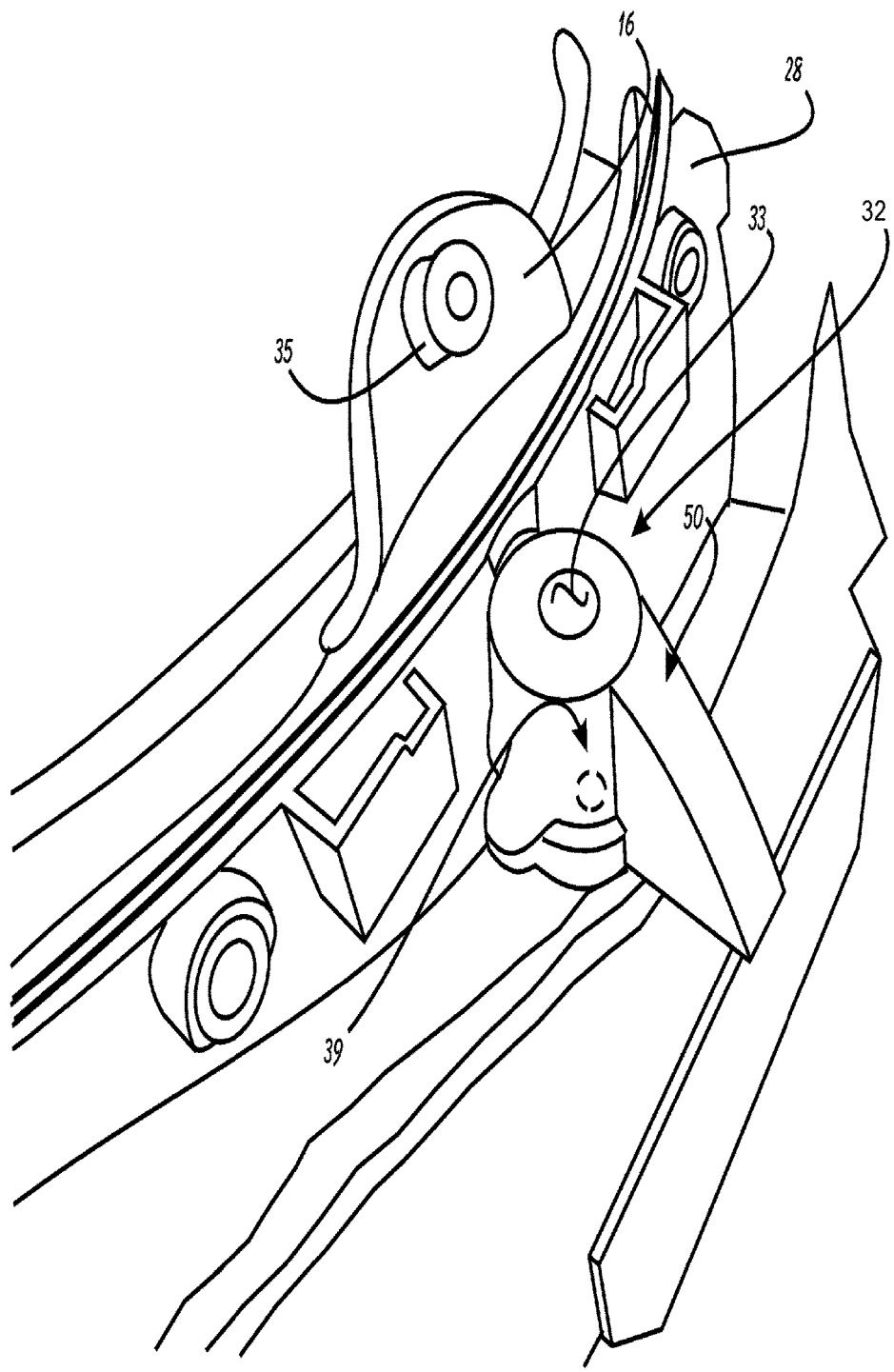
FIG. 9 is partial perspective view of the fluid storage components dispersed on the rear housing member of the device of FIG. 1.

FIG. 5 is a top perspective view of the gasket and rear housing members 22, 28 of the device [10] of FIG. 1. The rear housing member 28 defines a treatment chamber 14 within it. The therapeutic mist/vapor is injected into this region when the mask assembly [17] is attached to the user's head. As discussed previously, the gasket member 22 and fill port lid 16 are molded from a single piece of pliable material that attaches to the inside/back-side of the rear housing member 28. From the top, as depicted in FIG. 6, the treatment chamber 14 can be seen to be elongate side-to-side, and to have a notch 36 formed in its bottom wall to accommodate the users' nose (actually the bridge area of the nose) therein, so that the back face of the treatment chamber will closely form (via the gasket member [22]) to virtually all potential users' faces. Also shown here is the heating element 42, which extends across the front wall 38 of the treatment chamber 14. Activating this element will warm the interior of the treatment chamber 14. The mist conduit (not shown) may also pass through this or another heating element so that the incoming mist could also be heated (by this element 42, or via a separate element dedicated to the mist conduit (not shown)). FIGS. 7, 8 and 9 provide additional detail about the internal components of the mask assembly [17].

FIG. 7 is a partial right perspective view of the rear housing member 28 and FIG. 8 is a partial left perspective view of the rear housing member 28. First and second massage assemblies 44A, 44B are attached to the rear housing member 28 at the left and right corners thereof (additional assemblies of similar configuration could be located elsewhere within the mask assembly [17]). These assemblies 44A, 44B generate vibrations when in operation. These vibrations are transmitted through the rear housing member 28 to the gasket member [22], such that the user feels a soothing massaging sensation in their upper facial area.

Each massage assembly 44A, 44B comprises an electric massage motor 45A, 45B that has a rotating shaft, to which an offset weight element 48A, 48B is attached. The offset weight element 48A, 48B is, as its name conveys, a weight that is not distributed symmetrically around the axis of rotation of the motor 45A, 45B shaft. When the motor 45A, 45B drives the shaft to rotate (i.e. in direction "R"), the rotation of the weight elements 48A, 48B will generate vibrations. As discussed above, these vibrations will transmit through the rear housing member 28 and gasket member [22], and to the user's skin.

Figure 10:
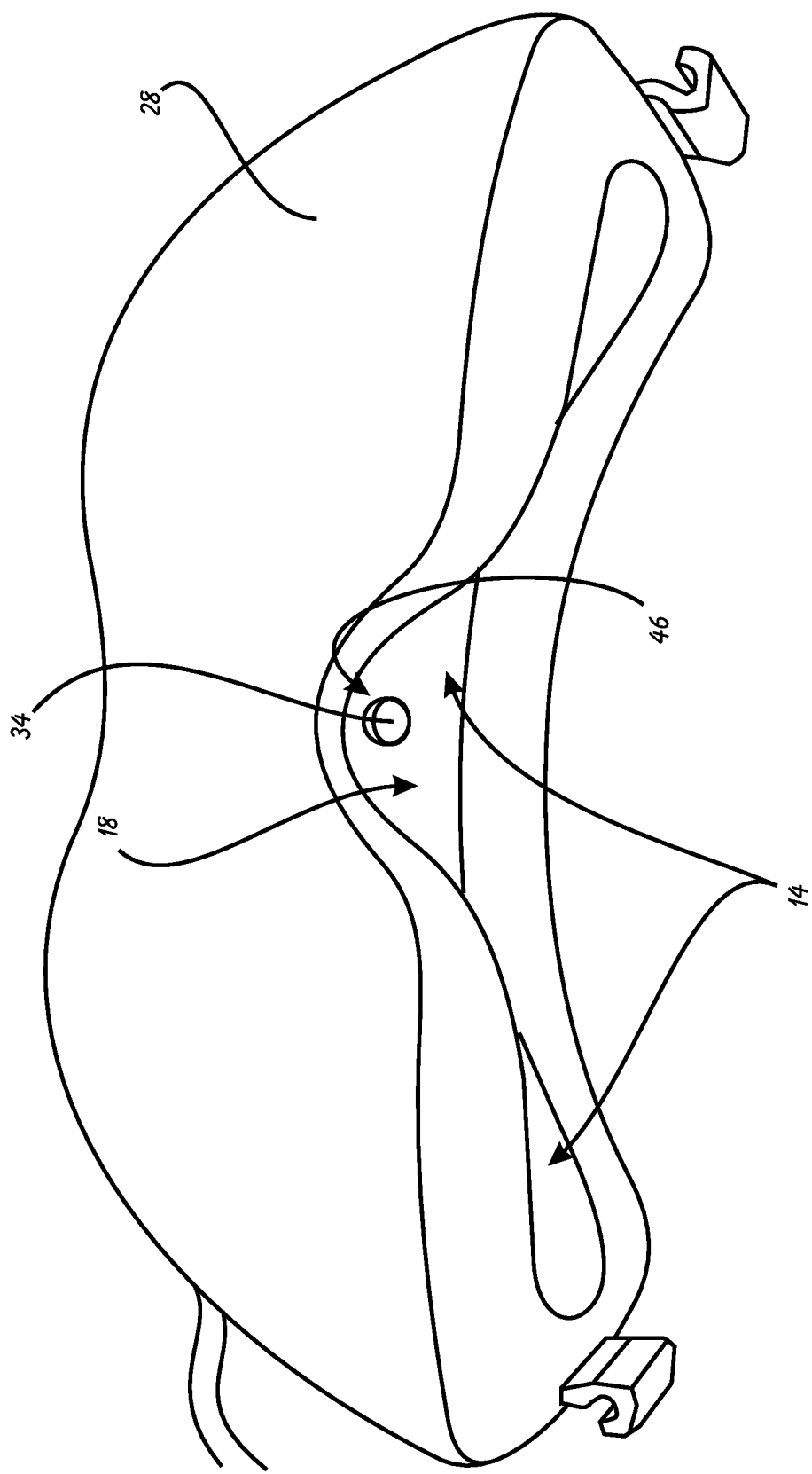
FIG. 10 is a bottom view of the rear housing member of the device of FIG. 1.

Turning to FIGS. 9 and 10, we can examine the way in which this device generates its mist and introduces it into the treatment chamber 14. FIG. 9 is partial perspective view of the fluid storage components dispersed on the rear housing member 28 of the device [10] of FIG. 1. A fluid chamber 32 is attached to the central top area of the rear housing member 28. The fill port 33 (aperture) is formed in the top of the chamber 32, and is sealable by the fill plug 35 and fill port lid 16, as discussed previously.

When the front cover [20] is attached to the rear housing member 28, the fill port 33 is lined up with the fill access aperture [30]. In this version, an ultrasonic transducer 34 (or other fluid vaporizing device) is located at the bottom of the fluid chamber 32. The transducer 34, when activated, agitates the fluid in the chamber 32 at a very high frequency until the fluid vaporizes. The fluid could be plain water, or water with essential oils, chemicals or other supplements blended in. In other versions (not depicted), other methods for liquid vaporization could be employed, such as ionic vibration and/or nanotechnology.

A liquid level chamber 50 extends from the main area of the fluid chamber 32. This chamber 50 has an arcuate shape on its front side that cooperates with the inner shape of the front cover [20]. When the front cover [20] is attached to the rear housing member 28, the liquid level chamber 50 will be viewable through the liquid level window [26] formed in the front cover [20].

One or more mist orifices 46 are formed through the roof 18 of the treatment chamber 14. The cool or hot vapor/mist is introduced into the treatment chamber 14 through the orifice(s) 46. In this version, the transducer 34 (and fluid chamber [32]) is positioned directly above the mist orifice 46, so that it generates mist directly into the chamber 14. In other versions, a mist conduit such as disclosed in the parent applications could be used.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A vaporizer device for treating skin surrounding an eyeball of a human face, the device comprising:
a main housing comprising a front cover attached to a rear housing member, a treatment chamber formed within the rear housing member, said treatment chamber comprising a concave chamber open on a back side of the rear housing member, wherein the back side of the rear housing member faces away from the front cover, a nose notch disposed on a bottom wall of the treatment chamber;
one or more massage motors attached to said treatment chamber, each of said one or more massage motors generating a vibratory motion in said treatment chamber when activated;
a fluid chamber contained within said main housing;
a mist generating device in fluid communication with said fluid chamber;
a mist conduit interconnecting said mist generating device with at least one orifice formed in a roof of said treatment chamber, the roof being opposite the bottom wall;
a heating element located within said main housing and between said front cover and said rear housing member, and exterior to said treatment chamber, said heating element being in contact with said rear housing member, and external to said fluid chamber, whereby actuating said heating element heats said rear housing member, a front wall of said treatment chamber in spaced relation to said eyeball when said vaporizer device is worn on the human face; and
a pliable gasket member disposed on said rear housing member, said pliable gasket member shaped to conform to and encircle upper and outside portions of a human user's facial eye area, whereby the human user's eyeball is in fluid communication with said treatment chamber, whereby a heating of said treatment chamber with said heating element heats said user's face via conduction, wherein said fluid chamber is disposed at a central top area of the rear housing and is located on top of the mist generating device, wherein said fluid chamber is further defined by a fill port formed therein, said fill port sealed by a fill port lid formed as a part of said pliable gasket.

2. The device of claim 1, further comprising a mist heating element located within said main housing, and along said mist conduit, whereby actuating said mist heating element heats said mist conduit and any mist located therein.

3. The device of claim 1, wherein said front cover is further defined by a liquid level window formed therein, said liquid level window comprising a translucent portion of said front cover, said liquid level window and said fluid chamber cooperatively positioned such that liquid in said fluid chamber is viewable through said liquid level window.

4. The device of claim 1, wherein said front cover is further defined by a fill access aperture, said fill access aperture located such that said fill port is accessible therethrough when said front cover is attached to said treatment chamber.

5. The device of claim 1, wherein said treatment chamber is formed with an outer face defining an arcuate face wall encircling said treatment chamber, said pliable gasket only partially covering said arcuate face wall.

6. The device of claim 1, wherein said fill port lid and said pliable gasket member are a single unitary piece of pliable material.

7. The device of claim 1, further comprising a head strap element extending from said main housing, said head strap element provided to allow a user to attach said device to the user's head.

8. A skin treatment device for skin surrounding a user's eyeballs, the device comprising:
  a rear housing member shaped to fit over the user's eye area, a treatment chamber formed within the rear housing member, said treatment chamber comprising a concave chamber having a nose notch disposed on a bottom wall of the treatment chamber, a top wall of said treatment chamber comprising one or more mist orifices formed therethrough, wherein said top wall is disposed opposite of said bottom wall, said treatment chamber juxtaposed over said user's eyeballs when said treatment device is being worn such that mist emitted through said mist orifices will hydrate the skin surrounding said user's eyeballs;
  a heating element located in proximity to said treatment chamber and external to said treatment chamber, whereby actuating said heating element heats said rear housing member by thermal conduction;
  a pliable gasket member attached on said rear housing member whereby said pliable gasket member is between the user's face and a portion of said rear housing member when said device is being worn on the user's eye area;
  a fluid chamber attached to said rear housing member;
  a mist generating device in fluid communication with said fluid chamber, wherein said fluid chamber is disposed at a central top area of the rear housing and is located on top of the mist generating device, wherein said fluid chamber is further defined by a fill port formed therein, said fill port sealed by a fill port lid formed as a part of said pliable gasket;
  a mist conduit interconnecting said mist generating device and said one or more mist orifices; and
  a front cover attached to said rear housing member, whereby said heating element is enclosed between said front cover and said rear housing member.

9. The device of claim 8, wherein said treatment chamber is defined by an upper rim having an arcuate shape, a lower rim having said nose notch formed therein, and an eye chamber area formed between said upper rim and said lower rim, said eye chamber area defined by an upper wall adjacent to said upper rim, a lower wall adjacent to said lower rim, side walls and said front wall, and wherein:
  said pliable gasket member is attached to said upper rim; and
  said one or more mist orifices are formed in said upper wall.

10. The device of claim 9, further comprising one or more massage motors attached to said rear housing member between said rear housing member and said front cover, each of said one or more massage motors generating a vibratory motion in said rear housing member when activated to rotate.

11. The device of claim 10, wherein said front cover is further defined by a liquid level window formed therein, said liquid level window comprising a translucent portion of said front cover, said liquid level window and said fluid chamber cooperatively positioned such that liquid in said fluid chamber is viewable through said liquid level window.

12. The device of claim 11, wherein front cover is further defined by a fill access aperture, said fill access aperture located such that said fill port is accessible therethrough when said front cover is attached to said treatment chamber.

13. The device of claim 12, wherein said fill port lid and said pliable gasket member are a single unitary piece of pliable material.

14. The device of claim 9, further comprising a mist heating element attached to said rear housing member, and along said mist conduit, whereby actuating said mist heating element heats said mist conduit and any mist located therein.

15. A wearable device for treatment of skin surrounding an eyeball of a face, the device comprising:
  a rear housing member shaped to fit in a position juxtaposed over a user's eye area, a treatment chamber formed within the rear housing member, said treatment chamber comprising a concave chamber, a nose notch on a bottom wall of the treatment chamber, a top wall of said treatment chamber comprising one or more mist orifices formed therethrough, and a back wall of said treatment chamber opposing the eyeball whereby said back wall is in spaced relation to the eyeball when worn, whereby mist emitted through said orifices will be applied to said skin surrounding the eyeball of the face;
  a pair of massage assemblies attached to said rear housing member, each of said pair of massage assemblies comprising an electric motor from which a rotatable shaft extends, and an offset weight element attached to said shaft;
  a pliable gasket member attached on said rear housing member whereby the pliable gasket member is between the user's face and said rear housing member when said device is being worn on the user's eye area;
  a fluid chamber attached to said rear housing member;
  a mist generating device in fluid communication with said fluid chamber, wherein said fluid chamber is disposed at a central top area of the rear housing and is located on top of the mist generating device, wherein said fluid chamber is further defined by a fill port formed therein, said fill port sealed by a fill port lid formed as a part of said pliable gasket;
  a mist conduit interconnecting said mist generating device and said one or more mist orifices;
  a heating element attached to said rear housing member, said heating element attached to said rear housing member whereby it provides heat to said rear housing member by thermal conduction when activated;
  a front cover attached to said rear housing opposite to said pliable gasket member; and
  a head strap element extending from opposite sides of said rear housing member.

* * * * *